US 9,431,387 B2

(12) United States Patent
Garner et al.

(10) Patent No.: US 9,431,387 B2
(45) Date of Patent: Aug. 30, 2016

(54) ELECTROSTATIC DISCHARGE PROTECTION

(71) Applicant: DNAE GROUP HOLDINGS LIMITED, London (GB)

(72) Inventors: David Garner, London (GB); Hua Bai, London (GB)

(73) Assignee: DNAE GROUP HOLDINGS LIMITED, London (GB)

( * ) Notice: Subject to any disclaimer, the term of this patent is extended or adjusted under 35 U.S.C. 154(b) by 0 days.

(21) Appl. No.: 14/937,847

(22) Filed: Nov. 10, 2015

(65) Prior Publication Data

US 2016/0064370 A1 Mar. 3, 2016

Related U.S. Application Data

(63) Continuation of application No. 13/878,323, filed as application No. PCT/GB2011/051920 on Oct. 6, 2011, now Pat. No. 9,209,170.

(30) Foreign Application Priority Data

Oct. 8, 2010 (GB) .................... 1016980.3

(51) Int. Cl.
  H01L 27/02 (2006.01)
  H01L 29/66 (2006.01)
  G01N 27/414 (2006.01)
(52) U.S. Cl.
  CPC ....... *H01L 27/0251* (2013.01); *G01N 27/4148* (2013.01); *H01L 27/0288* (2013.01); *H01L 27/0292* (2013.01); *H01L 29/66825* (2013.01)

(58) Field of Classification Search
  USPC .......................................... 361/56
  See application file for complete search history.

(56) References Cited

U.S. PATENT DOCUMENTS

| 4,282,540 | A | 8/1981 | Ning et al. |
| 4,288,256 | A | 9/1981 | Ning et al. |
| 8,354,316 | B2 | 1/2013 | Bhalla et al. |
| 2007/0262358 | A1 | 11/2007 | Burgmair et al. |
| 2008/0094074 | A1 | 4/2008 | Kim et al. |
| 2008/0111161 | A1 | 5/2008 | Sorge et al. |
| 2009/0026082 | A1 | 1/2009 | Rothberg et al. |
| 2009/0127589 | A1 | 5/2009 | Rothberg et al. |

(Continued)

FOREIGN PATENT DOCUMENTS

| DE | 10 2006 052863 | 5/2008 |
| EP | 1 729 121 | 12/2006 |
| WO | 2005/075969 | 8/2005 |

OTHER PUBLICATIONS

Int'l Search Report for PCT/GB2011/051920, four pages, dated Dec. 28, 2011.

(Continued)

*Primary Examiner* — Thienvu Tran
*Assistant Examiner* — Angela Brooks
(74) *Attorney, Agent, or Firm* — Nixon & Vanderhye PC

(57) ABSTRACT

A device comprising an electrostatic discharge protection structure, an ion sensitive field effect transistor (ISFET) having a floating gate, and a sensing layer located above the floating gate. The device is configured such that the electrical impedance from the sensing layer to the electrostatic discharge protection structure is less than the electrical impedance from the sensing layer to the floating gate. The device can be fabricated in a standard CMOS process.

17 Claims, 8 Drawing Sheets

(56) References Cited

U.S. PATENT DOCUMENTS

| | | | |
|---|---|---|---|
| 2010/0137143 A1* | 6/2010 | Rothberg | C12Q 1/6874 |
| | | | 506/2 |
| 2011/0204455 A1* | 8/2011 | Kang | G01N 27/4148 |
| | | | 257/414 |
| 2011/0263463 A1 | 10/2011 | Rothberg et al. | |
| 2011/0275522 A1 | 11/2011 | Rothberg et al. | |
| 2011/0281737 A1 | 11/2011 | Rothberg et al. | |
| 2011/0281741 A1 | 11/2011 | Rothberg et al. | |
| 2011/0299337 A1* | 12/2011 | Parris | H01L 28/40 |
| | | | 365/185.18 |
| 2015/0171018 A1 | 6/2015 | Hoque et al. | |

OTHER PUBLICATIONS

Written Opinion for PCT/GB2011/051920, seven pages, dated Dec. 28, 2011.

Int'l Preliminary Report on Patentability for PCT/GB2011/051920, nine pages, dated Dec. 3, 2012.

The ISR, written opinion, and IPRP provide a concise explanation of the relevance of the non-English foreign patent documents.

* cited by examiner

ELECTROSTATIC DISCHARGE PROTECTION

This application is a continuation of application Ser. No. 13/878,323, filed Apr. 8, 2013, now allowed; which is the U.S. national stage of Application No. PCT/GB2011/051920, filed Oct. 6, 2011; the contents of each of which are incorporated herewith by reference.

FIELD OF THE INVENTION

The invention relates to electrostatic discharge protection for ion sensitive field effect transistors. The invention may be relevant in particular, though not necessarily, in providing electrostatic discharge protection for ion sensitive field effect transistors fabricated using CMOS technology.

BACKGROUND

Electrostatic Discharge (ESD) is the sudden flow of electric current between two objects at different electric potentials. This is usually due to a build up of charges on one of the objects (or opposite charges on the two objects), which is discharged when the objects come into contact or close proximity. When the electrical field between two objects is sufficient to cause dielectric breakdown in the air separating them, a spark occurs. However, ESD can occur less noticeably when two objects simply contact and the potential difference is simply discharged through conduction. Static build up commonly builds up through tribocharging, which is the separation of charges when two contacting objects are separated.

ESD is a major concern in the use and manufacture of electrical and electronic goods. The sudden discharge of a potential difference of even 12v can destroy some devices such as transistors. In manufacturing, a typical solution is to ground all components including the operator and tools such that any static is discharged to ground through wire straps.

Ion Sensitive Field Effect Transistors (ISFET) (including Chemically sensitive Field Effect Transistors (ChemFET) and Enzyme Field Effect Transistors (EnFET)) are transistors designed to detect a species in a fluid sample. The charge of the species in proximity or contact with the transistor affects the operation of the transistor, which can be monitored using electrical instrumentation. The top layer of the transistor may be coated with a sensing layer to target a particular species.

Such transistors suffer from ESD, particularly those featuring a floating gate structure. As the name implies, a floating gate, is not electrically connected to the remaining parts of the transistor, so as to make the gate sensitive to ion charges. However this also makes the structure vulnerable to ESD strikes which may leave residual charges in the structure. The electrostatic discharge (ESD) event will cause a charge to be trapped in the floating gate, causing a large threshold voltage shift of the ISFET and even non-reversible damage to the device. Once the threshold voltage shifts, it increases the difficulty of instrumentation design to read the proper threshold voltage in the expected range. ESD can also damage ISFETs by physically and chemically degrading materials or leaving residual charges on various structures such as oxides. As a result, a form of ESD protection for ISFETs is very necessary.

WO9520243 (Baxter) discloses a protection circuit for an ISFET to protect the device from an ESD event to the liquid. The circuit is made up of conventional protective elements, integrated onto a silicon chip in a non-CMOS process.

The known ESD protection schemes either fail to provide sufficient protection or require extra manufacturing steps after a standard CMOS process, making the device costly. The present inventors have appreciated this problem and invented a novel device that provides cost effective ESD protection in an unmodified CMOS process.

SUMMARY OF THE INVENTION

According to a first aspect of the invention there is provided a device comprising an electrostatic discharge protection structure, an ion sensitive field effect transistor (ISFET) having a floating gate, and a sensing layer located above the floating gate. The device is configured such that the electrical impedance from said sensing layer to the electrostatic discharge protection structure is less than the electrical impedance from said sensing layer to the floating gate.

According to a second aspect of the invention there is a method of fabricating a semiconductor device, the method comprising
1) depositing and selectively removing an insulating material to form a gate insulator;
2) depositing and selectively removing a conductive material to form a floating gate on top of the gate insulator;
3) depositing an insulating material on top of the floating gate;
4) subsequently depositing and selectively removing a conductive material to form an electrostatic protection structure;
5) depositing an insulating material on top of the electrostatic discharge protection structure; and
6) forming the sensing layer on the insulating material.

According to a third aspect of the invention there is provided a device comprising a semiconductor substrate and a multi-layered stratum . The multi-layered stratum comprises a sensing layer, a metal layer forming an electrostatic protection structure, and one or more metal layers forming a floating a floating gate structure. The electrostatic protection structure is at a layer between the floating gate structure and the sensing layer.

Preferred embodiments of the invention are set out in the accompanying dependent claims.

The invention therefore provides a robust ESD protection structure compatible with standard CMOS processing, without the need for additional post-processing steps.

BRIEF DESCRIPTION OF THE DRAWINGS

Specific embodiments of the invention will now be described by way of example only with reference to the accompanying figures, in which.

DETAILED DESCRIPTION

Several preferred embodiments providing Electrostatic Discharge (ESD) protection for Ion Sensitive Field Effect Transistors (ISFET) are presented below.

Figure 1:
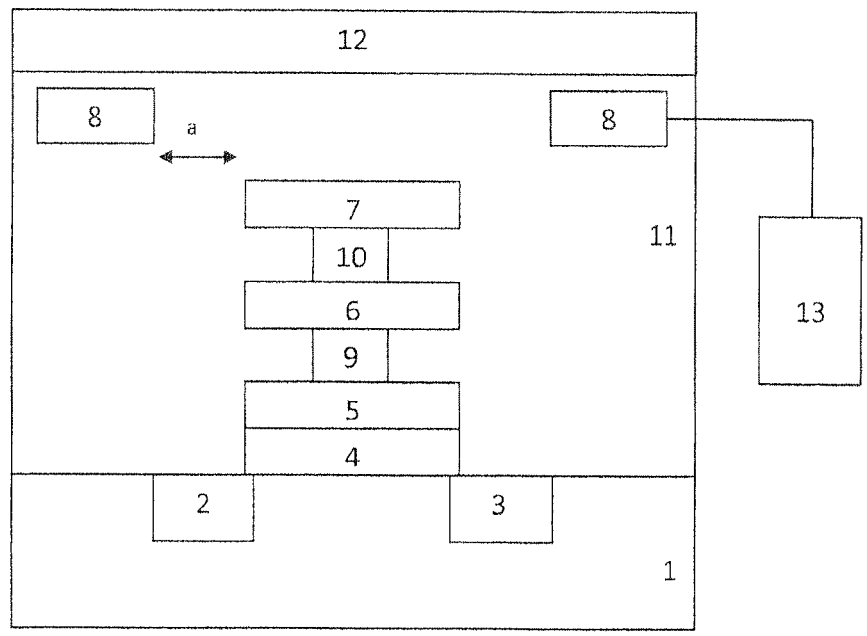
FIG. 1 is a cross-section illustration of an ISFET with a novel structure for ESD protection.

FIG. 1 shows a cross sectional illustration of a novel ISFET having a Floating Gate structure (5, 6, 7, 9 and 10) and a Guard Ring 8. It can be seen that the Guard Ring is located above the Floating Gate, and below the sensing layer 12 (which in this case is also the passivation layer designed to physically protect the semiconductor) of the device. During an ESD strike to the sensing layer 12, the path to the Guard Ring provides lower electrical impedance to the sensing layer than the Floating Gate, so that the strike is discharged to the Guard Ring rather than to the Floating Gate.

Such a device can be realised using a standard, unmodified CMOS process formed with the following steps:

Provide a substrate 1, for example a p-type silicon wafer approximately 1 mm thick;

Pattern and etch to form the gate oxide 4 (also called the intrinsic gate) which also defines and self-aligns the source 2 and drain 3;

Form source 2 and drain 3 diffusion regions in the substrate 1 using impurity ion diffusion;

Form a floating gate on top of the gate oxide with a polysilicon gate 5 and at least one metal layer (aluminium usually), with conducting vias connecting metal layers if more than one metal layer is used. Inter metal dielectric material can be deposited between and around metal layers for electrical insulation;

Form an ESD protection layer 8 in a metal layer above the floating gate layer(s), optionally connecting the layer 8 to electrical ground, typically via an ESD protection circuit 13;

Deposit a passivation layer 12 to protect the chip from mechanical handling and dicing. The passivation layer material may, for example, be Silicon nitride (Si3N4) or Silicon Oxynitride (SxNyO);

Optionally, deposit a selective sensing layer where the passivation layer material is not selective to the species of interest.

A reference electrode can be attached to the chip either externally or post-processed on chip to set the reference gate voltage for the ISFET.

The skilled person in CMOS fabrication techniques will appreciate that other standard steps will accompany those set out above to complete the device and that alternative processes and components exist. Such processes will develop and improve in time, such improvements still considered to be within the scope of the invention.

Typically, photolithography is used to build up the layers, transferring the circuit layout to the wafer. A mask, in cooperation with a UV-curable photoresist material, provides a pattern of the portions to be removed or built up. Material may be added to the wafer by known methods of deposition such as Plasma Enhanced Chemical Vapour Deposition (PECVD), Low Pressure Chemical Vapour Deposition (LPCVD), etc.

Photolithography, ion implantation, oxidation, etching and deposition methods are well known to persons skilled in CMOS processing but other techniques exist or may become available that are equally well suited to providing fabricating methods falling within the scope of the invention.

The metal layers are typically fabricated during 'back-end' processing. After the silicidation step covers the polysilicon and active areas with a thin layer of conductive material (such as metal), a layer of insulating material (such as an oxide) is deposited. Lithography combined with plasma etching can be used to remove oxide and form 'contact holes'. Metal is deposited on the oxide and also into the contact holes, forming a metal layer conductively coupled to the layer below. Further lithography removes unwanted portions of the metal to create the 'Metal 1 layer'. Further metal layers are created by repeating the steps of depositing an insulator, etching contact holes, depositing metal and etching the metal.

Note that while FIG. 1 shows a structure made from a 3-metal layer CMOS process (components 8, 7, 6 of FIG. 1), embodiments are not restricted to 3-metal layer processes.

In one embodiment, the device is formed in a CMOS process having multiple metal layers, the layer farthest from the intrinsic gate forming the Guard Ring, the layers nearest to the intrinsic gate forming the floating gate. In some embodiments the CMOS process has more than 3 layers, more than 4 layers, more than 5 layers, more than 6 layers, more than 7 layers, more than 8 layers, more than 9 layers, more than 10 layers, or more than 11 layers.

The Guard Ring may also comprise multiple layers and one or more layers may be at the same level as one or more floating gate layers, (the Guard Ring and Floating gate structures being laterally separated by insulating material).

An example implementation illustrated in FIG. 1 cross-section, shows an ESD protection structure 8 at least partially surrounding the floating gate structure. In plan view, the ESD structure forms a ring partially (FIG. 3) or completely (FIG. 2) encompassing the ISFET sensing gate. Portions of the Guard Ring are spaced apart, exposing the top layer of the floating gate to the ionic charges present at the passivation layer/sensing layer 12. The Guard Ring is closer to the sensing layer 12 than the floating gate structure top layer 7, such that the electrical impedance from the sensing layer to the Guard Ring is less than the electrical impedance from said sensing layer to the floating gate structure.

Figure 3:
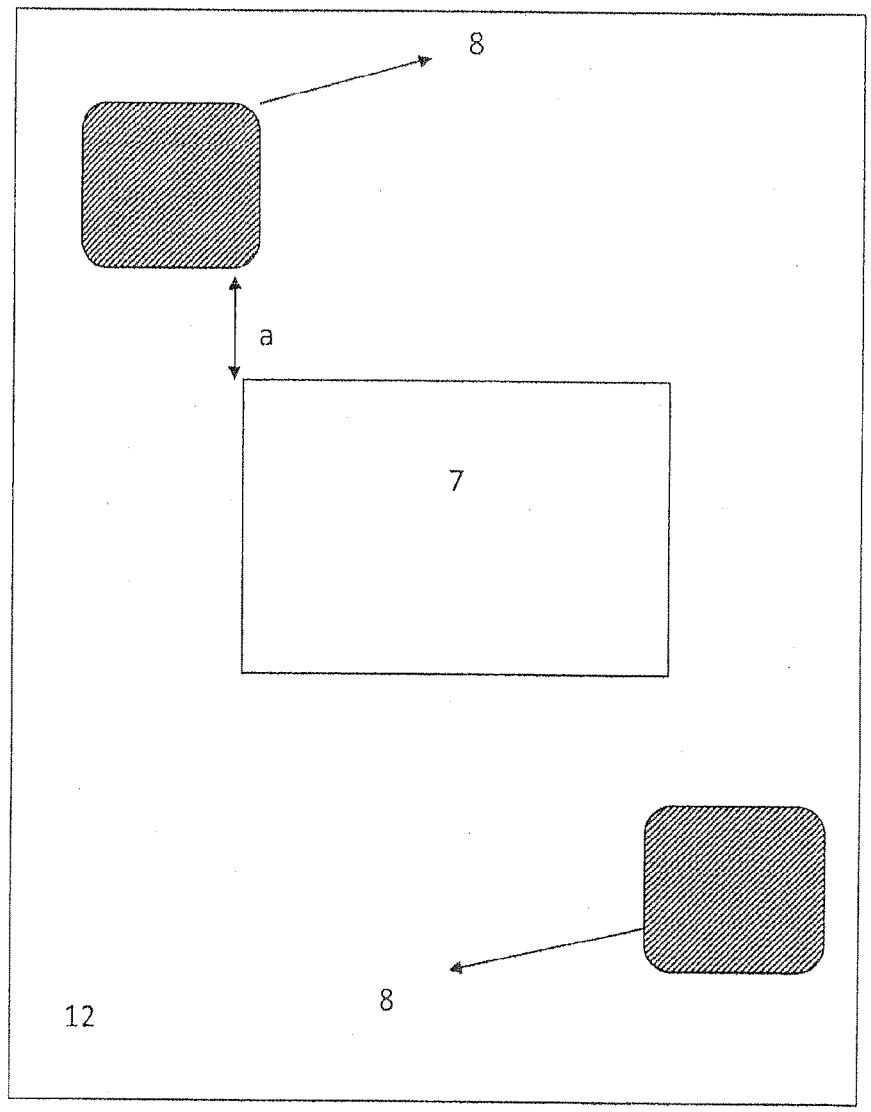
FIG. 3 is a plan view illustration of an ISFET having two Guard Pads.

As seen in FIG. 3, the ESD protection structure is not necessary in the format of a ring, but may be designed in an arbitrary shape. The shape may not fully encompass the ISFET sensing gate but is located close enough to the ISFET floating gate to provide a preferential path for an electro static strike. In some embodiments, the lateral distance (distance 'a' in FIGS. 1 and 3) between the said ESD protection structure and ISFET floating gate is preferably less than 0.5 um, less than 1 um, less than 2 um, less than 10 um, or less than 100 um. The closer the distance, the better the ESD protection.

When an ESD event happens, the charges will try to find the lowest impedance path to discharge. The Guard Ring 8 (e.g. implemented with Metal Layer 3) provides a much lower impedance path compared with the floating gate top layer 7 (e.g. implemented with Metal Layer 2). It is not necessary to connect the Guard Ring directly to ground, as long as there is provided a conductive path for the accumulated charges to dissipate when there is an ESD event. The conductive path could be made from one or more of the following: a metal conductor, a diode, a resistor, a thin oxide MOSFET or a capacitor, which could be internal to the CMOS chip or external to the CMOS chip. The devices from which the conductive path is fabricated are not limited to the aforementioned devices.

Figure 2:
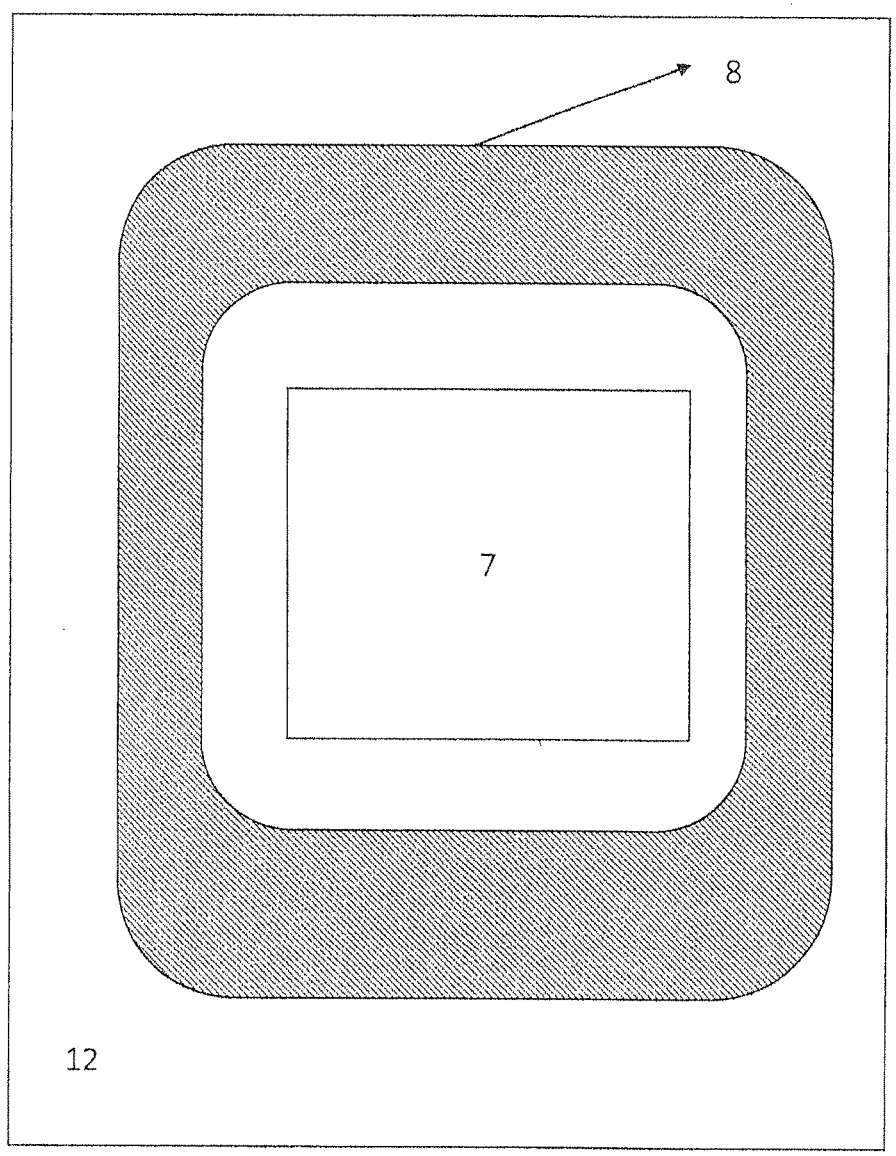
FIG. 2 is a plan view illustration of an ISFET with a novel structure for ESD protection.

FIG. 2 is a plan view illustration of an embodiment showing a Guard Ring 8 encompassing the top surface 7 of the floating gate structure. The fluid sample is in contact with the sensing layer 12 provided by the passivation layer. It will be appreciated that the components 8, 7, 12 are all at different layers. The shapes, relative sizes and positions shown are illustrative only.

Whilst dimensions of components of the device may vary considerably, certain dimensions will be dictated by the CMOS process used. In exemplary embodiments:

- the thickness of each metal layer is 0.5 um to 1.5 um;
- the width or diameter of the floating gate is 0.1 um to 1000 um;
- the lateral spacing 'a' between the edges of the Guard Ring and the floating gate is 0.1 um to 100 um (alternatively the edges of the Guard Ring and floating gate may overlap by up to 20%);
- the width of the Guard Ring is 0.1 um to 1000 um;
- the impedance between the Guard Ring 8 and the sensing layer 12 is less than 50% of the impedance between the floating gate 7 and the sensing layer 12, preferably less than 30% of the impedance between the floating gate and the sensing layer, more preferably less than 20% of the impedance between the floating gate and the sensing layer.

In another embodiment (shown in FIG. 3), the ESD protection structure comprises two or more ESD protection elements 8 allocated around the floating gate to be protected. The shapes, relative sizes and positions shown are illustrative only.

Figure 4:
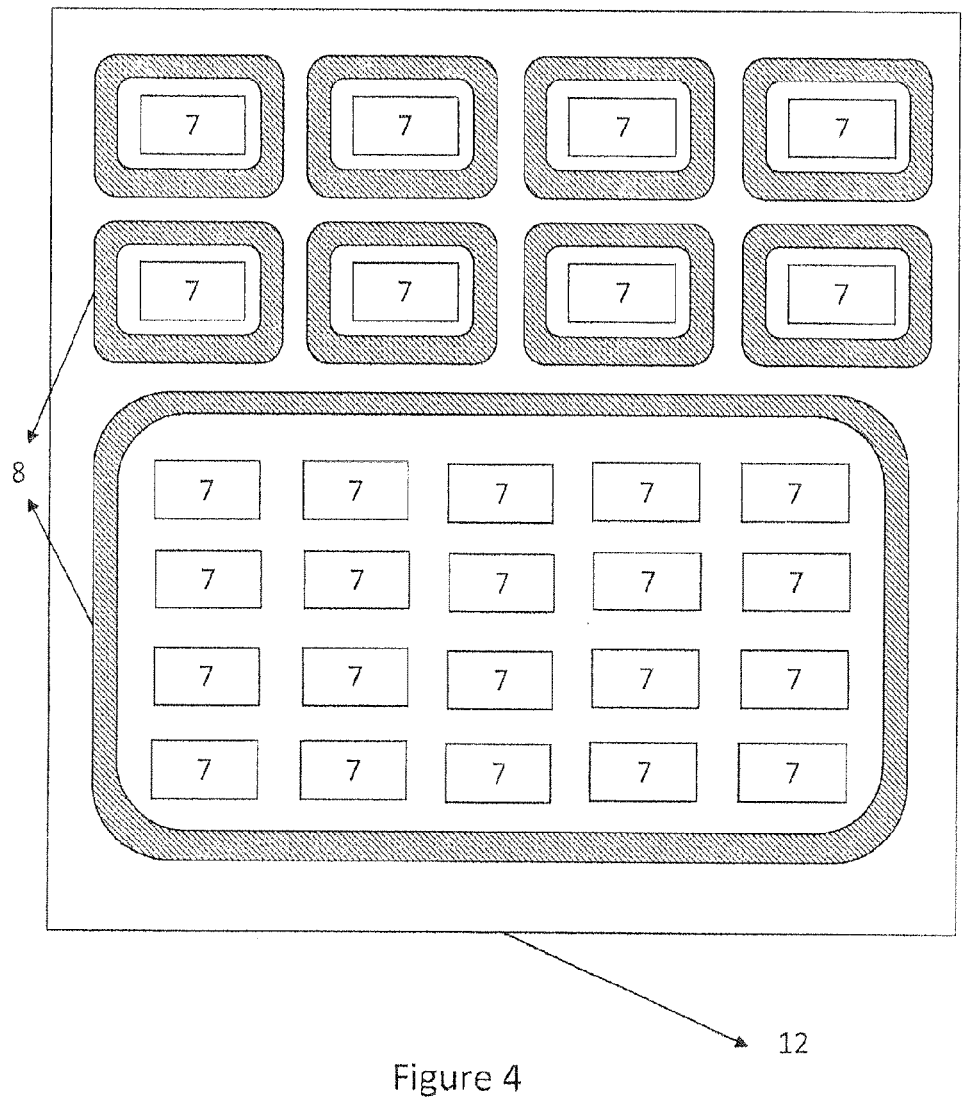
FIG. 4 is a plan view illustration of two arrays of ISFETs having different Guard Ring layouts.

An array may be formed comprising a plurality of ISFETs, for example 8 ISFETS, more than 10 ISFETS, more than 100 ISFETS, more than 1000 ISFETS, more than 10,000 ISFETS, or more than 100,000 ISFETS. A single ESD protection structure may protect several ISFETs or there may be one ESD protection structure for each ISFET, or there may be more than one ESD protection structure for each ISFET FIG. 4 illustrates a plan view exemplifying arrays of ISFETs. The top array of eight ISFETs shows each floating gate top layer 7 encompassed by a Guard Ring 8.

Figure 5:
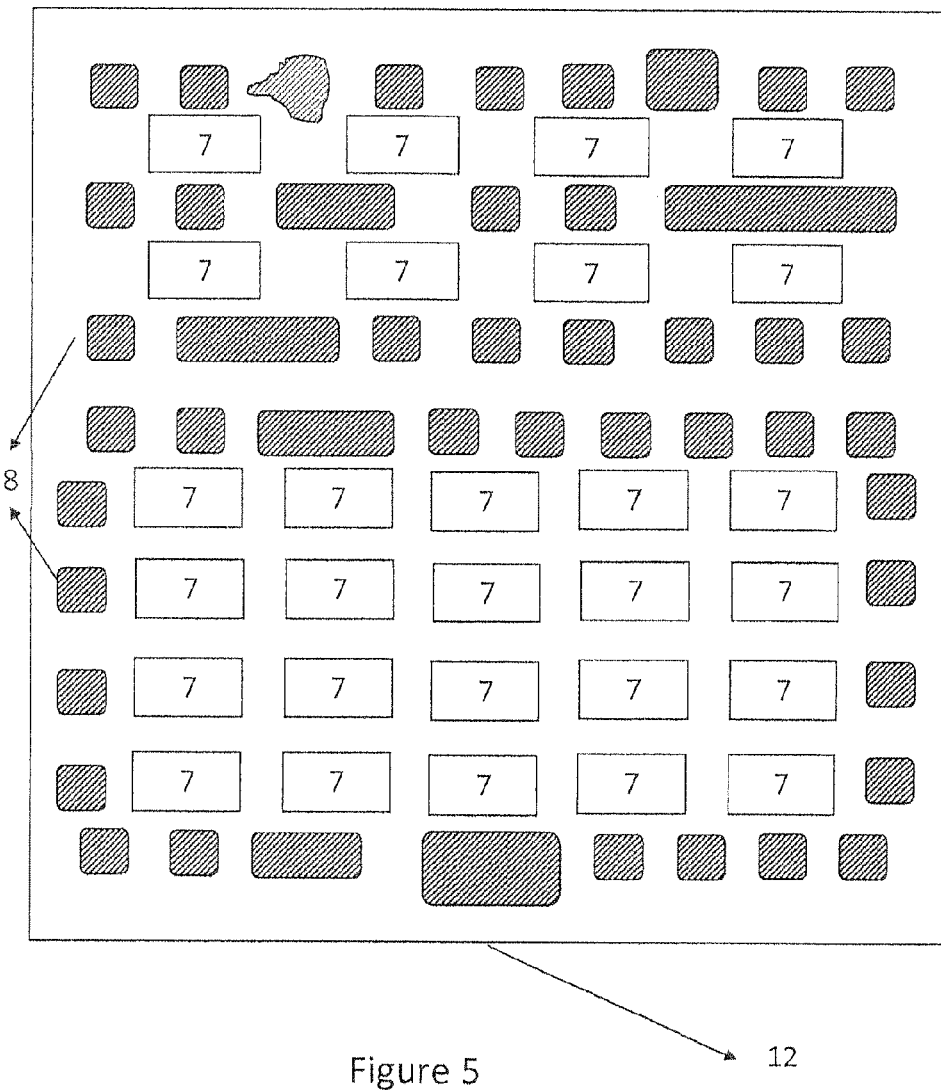
FIG. 5 is a plan view illustration of two arrays of ISFETs having different Guard Pad layouts.
Figure 6:
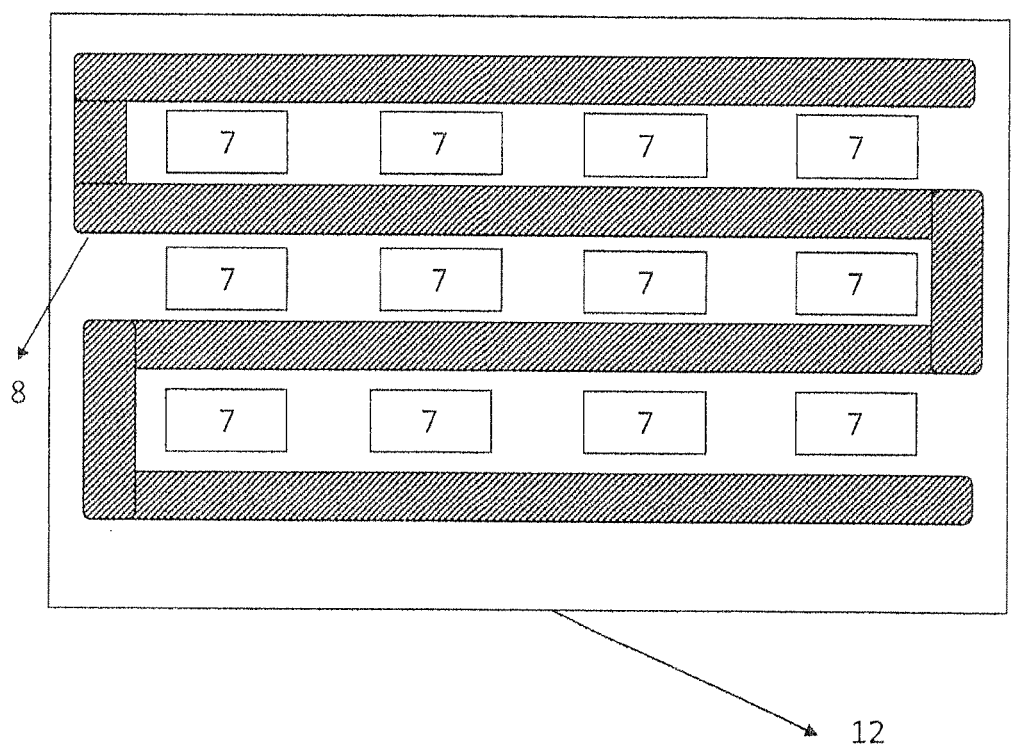
FIG. 6 is a plan view illustration of an array of ISFETs having a serpentine Guard structure.

The bottom array shows an alternative arrangement wherein a plurality of floating gates are encompassed by a Guard Ring 8. FIG. 5 illustrates how the ESD protection structures 8 may comprise pads of arbitrary shape distributed around one or more floating gate structures to be protected. FIG. 6 illustrates that the ESD protection structure may comprise a continuous area passing next to substantially all ISFETs of the array.

In use, the sensing layer 12 of the ISFET or array of ISFETs is arranged to come into contact with a fluid sample. Typically there will be a microfluidic structure for routing or containing the fluids as desired relative to the ISFETs. The sample will contain a concentration of ions, which can be detected by the ISFET in the usual way. If an ESD strike occurs in the fluid or microfluidic structure, the sensing layer 12 will experience a high static potential. The ESD protection structure 8 protects the ISFETs by providing a lower impedance to the surface than the floating gate surface 7. The ESD protection structure 8 accepts the charge and preferably provides a low impedance path to route it to ground (e.g. via a connected circuit 13).

Figure 8:
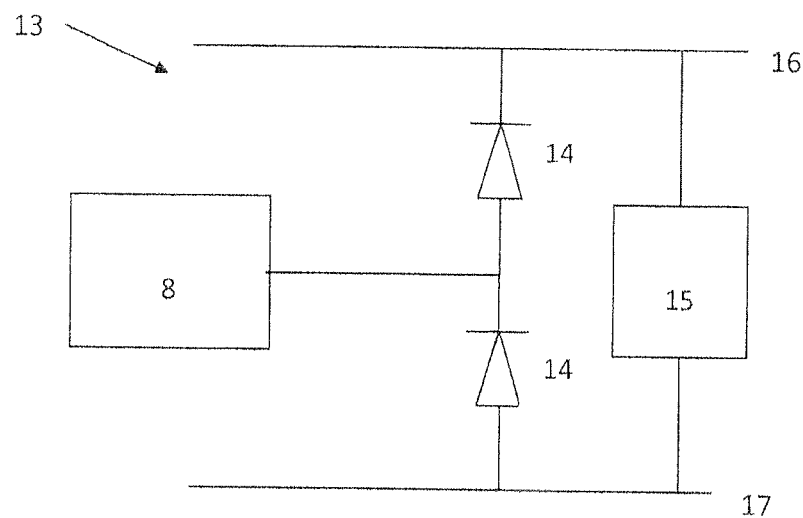
FIG. 8 is circuit diagram of a protection circuit.

A discharge circuit 13 may be coupled to the Guard Ring 8 to provide a controlled conduit to ground. FIG. 8 shows a protection circuit embodiment having diodes 14 for discharging a charge on the Guard Ring to either of the power supply voltages rails Vdd or Vss, the direction of discharge depending on the polarity of the static charge. The Rail Clamp Circuit 15 prevents the power supply from shorting, by discharging any static charge between the power supply rails.

Figure 7:
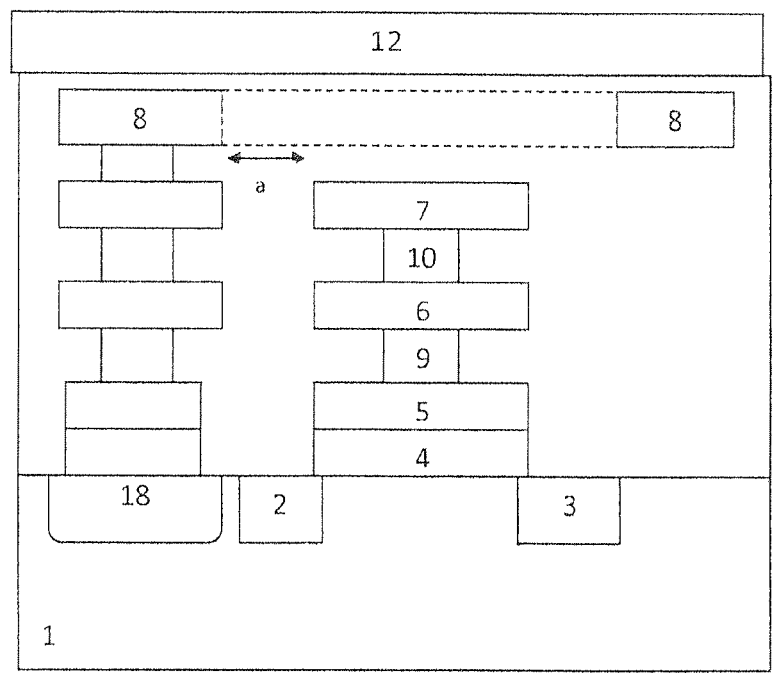
FIG. 7 is a cross-section view of an ISFET showing the ESD protection structure connected to the substrate.

In a preferred embodiment, the ESD structure is connected to the substrate through a series of interconnect vias and metal layers. The substrate itself may then be grounded or connected to a discharge circuit. FIG. 7 is a cross-section of such an embodiment. The connection of the ESD structure to the substrate may be to a well 19 in the substrate to create a diode junction. Each ESD element 8 may be connected to the substrate through these vias and metal layers or an ESD element 8 connected to the substrate may also be connected to further ESD elements.

The following components are shown in the accompanying drawings:

1. Silicon substrate
2. Source diffusion region
3. Drain diffusion region
4. Gate oxide
5. Polysilicon gate
6. Floating gate formed from Metal 1
7. Floating gate formed from Metal 2
8. ESD protection ring formed from Metal 3
9. Metal 1 to poly1 contact
10. Metal 2 to Metal 1 contact
11. Inter metal dielectrics
12. Top passivation layer/sensing layer
13. ESD discharge circuit
14. Diode
15. ESD Rail clamp circuit
16. Vdd
17. Vss
18. Well in substrate Preferable embodiments may have one or more of the following attributes:

The ESD protection structure is the shape of a ring.

The ESD protection structure is a continuous area passing next to substantially all ISFETs of the array.

The ESD protection structure is formed from one or more conductive elements placed proximate the ISFET device where said conductive elements do not form a closed ring around the floating gate of the ISFET device.

The ring has the thickness of one metal layer; the width may be of a similar magnitude.

The ring may be open or closed ended; and in plan view may be circular, rectangular, or generally follow the contour of the floating gate.

The invention claimed is:

1. A device comprising an electrostatic discharge protection structure, an ion sensitive field effect transistor (ISFET) having a floating gate, and a sensing layer located above the floating gate, the device being configured such that the electrical impedance from said sensing layer to the electrostatic discharge protection structure is less than the electrical impedance from said sensing layer to the floating gate and wherein the device is configured such that, in use, said sensing layer contacts a fluid sample.

2. A device according to claim 1, wherein the device has a planar, layered structure and the electrostatic discharge protection structure being located in a plane between the sensing layer and the floating gate.

3. A device according to claim 1, wherein the sensing layer is closer to the electrostatic protection structure than to the floating gate.

4. A device according to claim 1, wherein said floating gate and electrostatic discharge protection structure are each provided by one or more planar metal structures.

5. A device according to claim 1, wherein the sensing layer is a passivation layer.

6. A device according to claim 5, wherein the passivation layer is comprised of silicon nitride.

7. A device according to claim 1, wherein the electrostatic discharge protection structure is in the form of a substantially planar closed loop track.

8. A device according to claim 7, wherein a planar width of the closed loop track is greater than a planar width of the floating gate.

9. A device according to claim 1, wherein the electrostatic discharge protection structure comprises a plurality of discrete conductive elements.

10. A device according to claim 1, wherein the electrostatic discharge protection structure is coupled to an electrical ground and/or to an electrical power supply rail of the device via one or more elements selected from the group consisting of: a passive conduction component, a rail clamp circuit, and a diode.

11. A device according to claim 1, wherein the electrostatic discharge protection structure is not connected directly to ground.

12. A device according to claim 1, wherein the electrostatic discharge protection structure is connected to a conductive path configured to enable the accumulated charges to dissipate.

13. A device according to claim 12, wherein the conductive path is made from one or more of the following: a metal conductor, a diode, a resistor, a thin oxide MOSFET, or a capacitor.

14. A device according to claim 13, wherein the device is formed in a CMOS chip and the metal conductor, diode, resistor, thin oxide MOSFET, or capacitor is internal to the CMOS chip.

15. A device according to claim 13, wherein the device is formed in a CMOS chip and the metal conductor, diode, resistor, thin oxide MOSFET, or capacitor is external to the CMOS chip.

16. A device according to claim 1, further comprising a substrate base connected to the electrostatic discharge protection structure.

17. A device according to claim 16, wherein the substrate is electrically connected to ground.

* * * * *